US012758298B2

(12) United States Patent
Szabo

(10) Patent No.: US 12,758,298 B2
(45) Date of Patent: Oct. 13, 2026

(54) VESSEL SEALER WITH SLOT FOR REMOVAL OF DEBRIS

(71) Applicant: Conmed Corporation, Largo, FL (US)

(72) Inventor: Aaron Szabo, Swanton, OH (US)

(73) Assignee: Conmed Corporation, Largo, FL (US)

( * ) Notice: Subject to any disclaimer, the term of this patent is extended or adjusted under 35 U.S.C. 154(b) by 775 days.

(21) Appl. No.: 17/798,242

(22) PCT Filed: Feb. 5, 2021

(86) PCT No.: PCT/US2021/016758
§ 371 (c)(1),
(2) Date: Aug. 8, 2022

(87) PCT Pub. No.: WO2021/558880
PCT Pub. Date: Aug. 12, 2021

(65) Prior Publication Data
US 2023/0072071 A1 Mar. 9, 2023

Related U.S. Application Data

(60) Provisional application No. 62/970,905, filed on Feb. 6, 2020.

(51) Int. Cl.
*A61B 18/14* (2006.01)
*A61B 18/00* (2006.01)

(52) U.S. Cl.
CPC ................................ *A61B 18/1445* (2013.01); *A61B 2018/00601* (2013.01); *A61B 2018/00607* (2013.01);
(Continued)

(58) Field of Classification Search
CPC ...... A61B 18/1445; A61B 2018/00601; A61B 2018/00607; A61B 2018/0063; A61B 2018/1455
See application file for complete search history.

(56) References Cited

U.S. PATENT DOCUMENTS

2002/0115997 A1 8/2002 Truckai et al.
2011/0251612 A1 10/2011 Faller et al.
(Continued)

OTHER PUBLICATIONS

International Search Report Form PCT/ISA/220, International Application No. PCT/US2021/016758, pp. 1-16, Dated Apr. 27, 2021.

*Primary Examiner* — Joseph A Stoklosa
*Assistant Examiner* — William Mossbrook
(74) *Attorney, Agent, or Firm* — Bond, Schoeneck & King, PLLC; David L. Nocilly

(57) ABSTRACT

A surgical instrument that will automatically clear any debris from a knife pathway in response to normal operation of the knife. The instrument has a pair of jaws formed from a first jaw member and a second jaw member that are pivotally mounted with respect to each other for movement between an open position and a closed position. The jaw members support sealing surfaces that have tracks formed therein to define a knife pathway for a knife blade used to sever sealed tissue that is trapped in the jaws. Each jaw member has a slot aligned with the distal end of the track to provide a point of egress for debris that accumulates in the knife track. As the knife is advanced along the knife pathway during normal operation, any debris will be driven toward the distal end of the knife pathway and out of the slots.

14 Claims, 9 Drawing Sheets

(52) U.S. Cl.
CPC ................. *A61B 2018/0063* (2013.01); *A61B 2018/1455* (2013.01)

(56) References Cited

U.S. PATENT DOCUMENTS

| | | | | |
|---|---|---|---|---|
| 2011/0251613 | A1 | 10/2011 | Guerra et al. | |
| 2012/0083783 | A1* | 4/2012 | Davison ............. | A61B 18/1445 606/45 |
| 2015/0374396 | A1 | 12/2015 | Strobl et al. | |
| 2018/0042632 | A1* | 2/2018 | Frushour ............ | A61B 17/2804 |

* cited by examiner

VESSEL SEALER WITH SLOT FOR REMOVAL OF DEBRIS

CROSS-REFERENCES TO RELATED APPLICATIONS

This application is a national stage application under 35 U.S.C. 371 based on international patent application PCT/US21/16758 filed on Feb. 5, 2021, which claims priority to U.S. Provisional Patent Application Ser. No. 62/970,905, filed on Feb. 6, 2020, the entireties of which are incorporated herein by reference.

BACKGROUND OF THE INVENTION

1. Field of the Invention

The present invention relates surgical instruments and, more specifically, to a vessel sealer having improved debris removal.

2. Description of the Related Art

Electrosurgical vessel sealers are surgical instruments that are used for the occlusion of blood vessels and halting of bleeding during surgical procedures. The electrodes of the vessel sealer are carried by a pair of opposing jaws and interconnected to an electrosurgical generator that can selectively supply radiofrequency (RF) energy to the electrodes. A user may close the jaws around a vessel to be sealed by squeezing a lever associated with a handle assembly. The vessel may then be sealed by supplying the RF energy to the clamped vessel and the vessel can be severed by extending a knife blade along tracks formed in the jaws. During repeated use, however, debris associated with sealing activities can accumulate in the knife track and inhibit the proper operation of the knife. Accordingly, there is a need for an approach that will allow any debris in the knife track to be easily expelled from a vessel sealer to ensure proper operation of the surgical instrument.

BRIEF SUMMARY OF THE INVENTION

The present invention is a surgical instrument having slots that allow for the automatic expulsion of debris from the knife pathway of a vessel sealer in response to normal operation of the knife blade. More specifically, the surgical instrument comprises a pair of jaws having a first jaw member and a second jaw member that are pivotally mounted with respect to each other for movement between an open position and a closed position. A first sealing surface is supported by the first jaw member and has a first track formed therein that extends from a first open end to a first closed end. A second sealing surface is supported by the second jaw member and has a second track formed therein that extends from a first open end to a first closed end and that will align with the first track when the pair of jaws are in the closed position to define a knife pathway. A first slot is formed in the first jaw member proximately to the first open end of the first knife track. A second slot is formed in the second jaw member proximately to the second open end of the second knife track. The first slot is in communication with the first track. The second slot is in communication with the second track. A knife blade is positioned in the knife pathway and moveable in the knife pathway toward the first closed end of the first track and the second closed end of the second track. Movement of knife blade in the knife pathway toward the first closed end of the first track and the second closed end of the second track will cause any debris in the knife pathway to be ejected from at least one of the first slot and the second slot. The first track and the second track may be curved.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
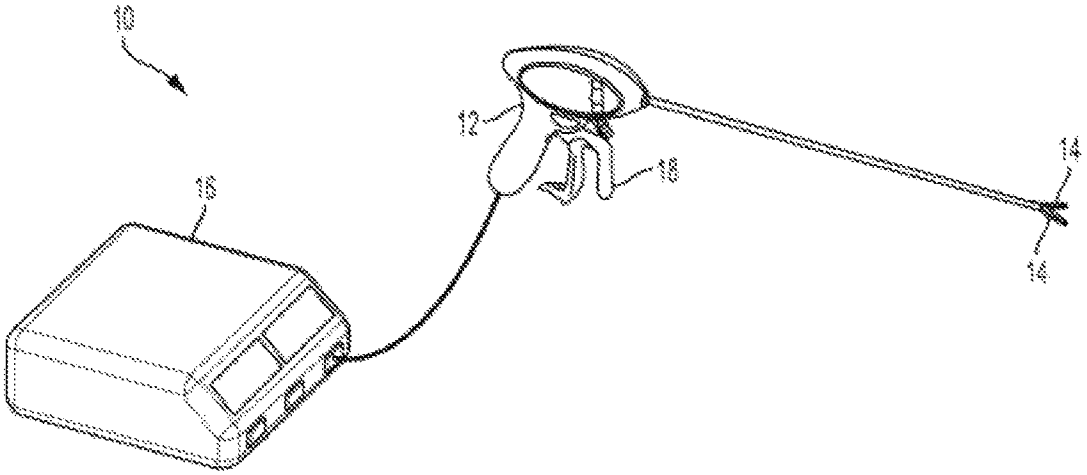
FIG. 1 is a perspective view of an electrosurgical system according to the present invention.

Referring to the figures, wherein like numeral refer to like parts throughout, there is seen in FIG. 1 an electrosurgical system 10 comprising a vessel sealer 12 having a pair of conductive opposing jaws 14 that are interconnected to an electrosurgical generator 16 that can supply RF energy to electrodes of jaws 14 for the desiccation of a blood vessel trapped between jaws 14. The dimensions of jaws 14 and the type of RF energy supplied will produce desiccation of the blood vessel in a region of a particular width as determined by the thermal spread of the energy being supplied to the blood vessel. As is known in the art, jaws 14 are pivotally mounted to vessel sealer 12 for movement between an open position and a closed position in response to a user operating a lever 18 extending from vessel sealer 12.

Figure 2:
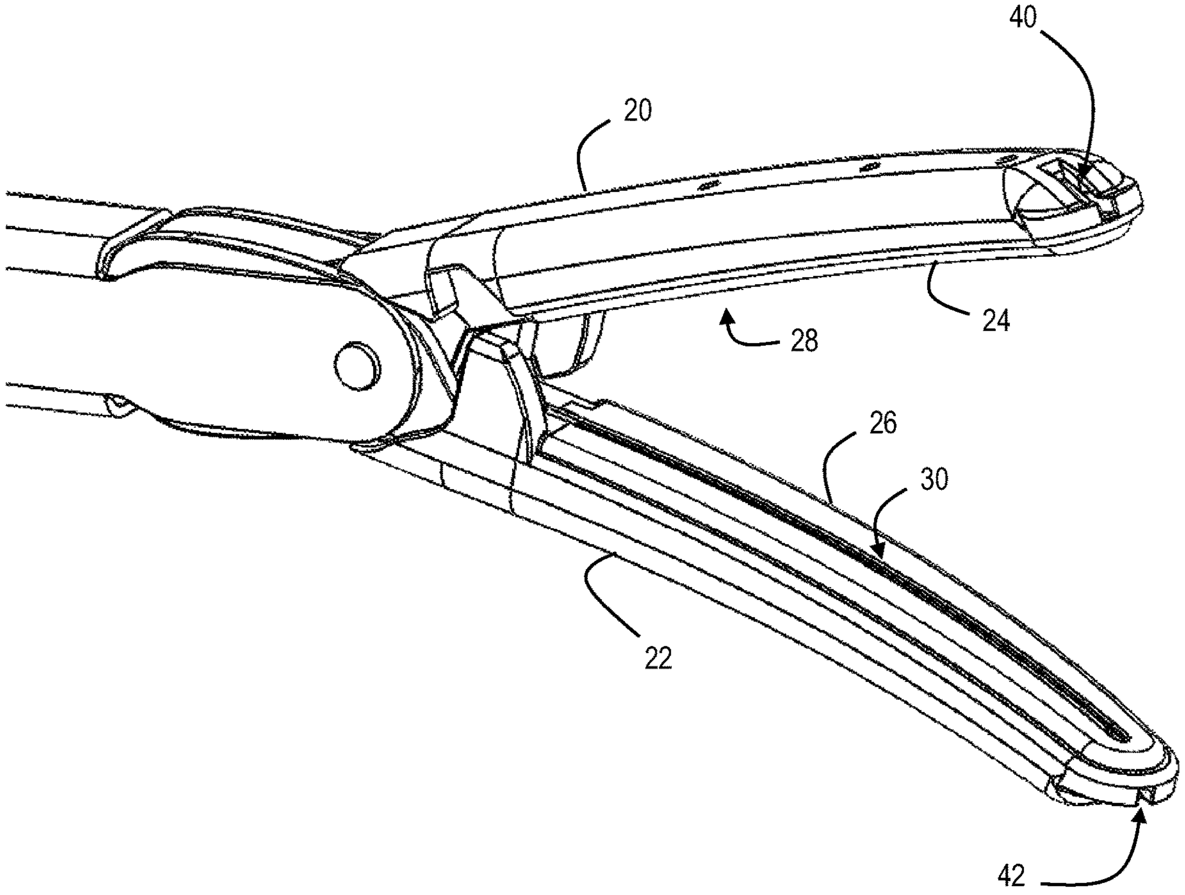
FIG. 2 is perspective view of the jaw of a vessel sealer according to the present invention.

Referring to FIG. 2, jaws 14 are comprised of two opposing jaw members 20 and 22. Jaw members 20 and 22 support inner conductive faces 24 and 26 that are electrically isolated from the rest of jaws 14 and sealer 12 and interconnected to electrosurgical generator 16. Inner conductive faces 24 and 26 have tracks 28 and 30 formed therethrough, respectively, so that when jaw members 20 and 22 are closed, tracks 28 and 30 align to define a knife pathway that intersects the region between jaw members 20 and 22 where tissue is desiccated between jaws 14 when they are energized. A knife blade 50 is aligned with and positioned in the knife pathway defined by tracks 28 and 30 and may be selectively extended through and withdrawn from the knife pathway, such as by a user operating a lever mounted to sealer 12, to sever any tissue trapped in jaws 14. The distal ends of tracks 28 and 30 are closed so that knife blade 50 cannot extend beyond jaw members 20 and 22 and conductive faces 24 and 26 encompass the distal tips of jaw members 20 and 22.

Figure 3:
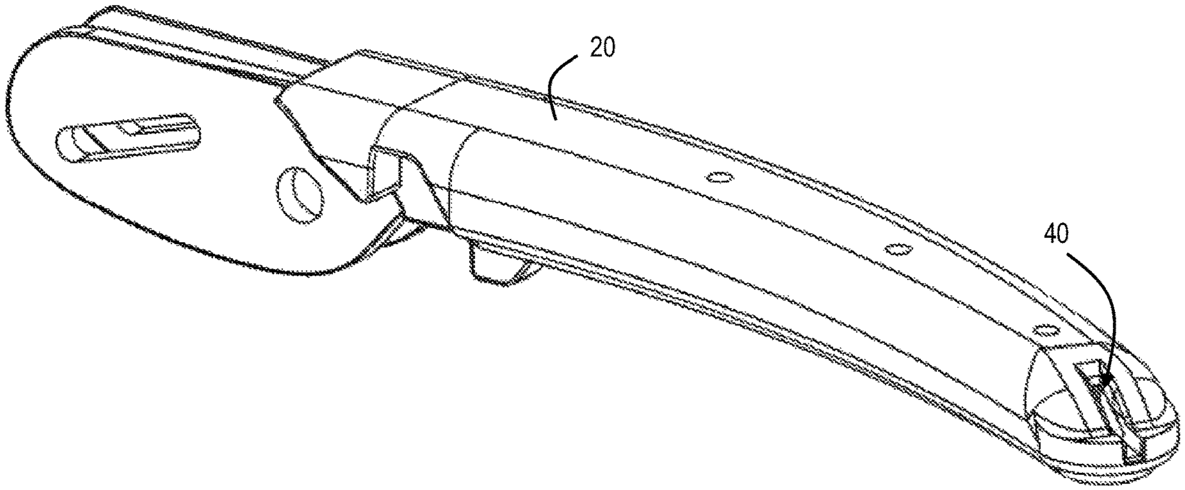
FIG. 3 is perspective view of a jaw member for a vessel sealer according to the present invention.
Figure 4:
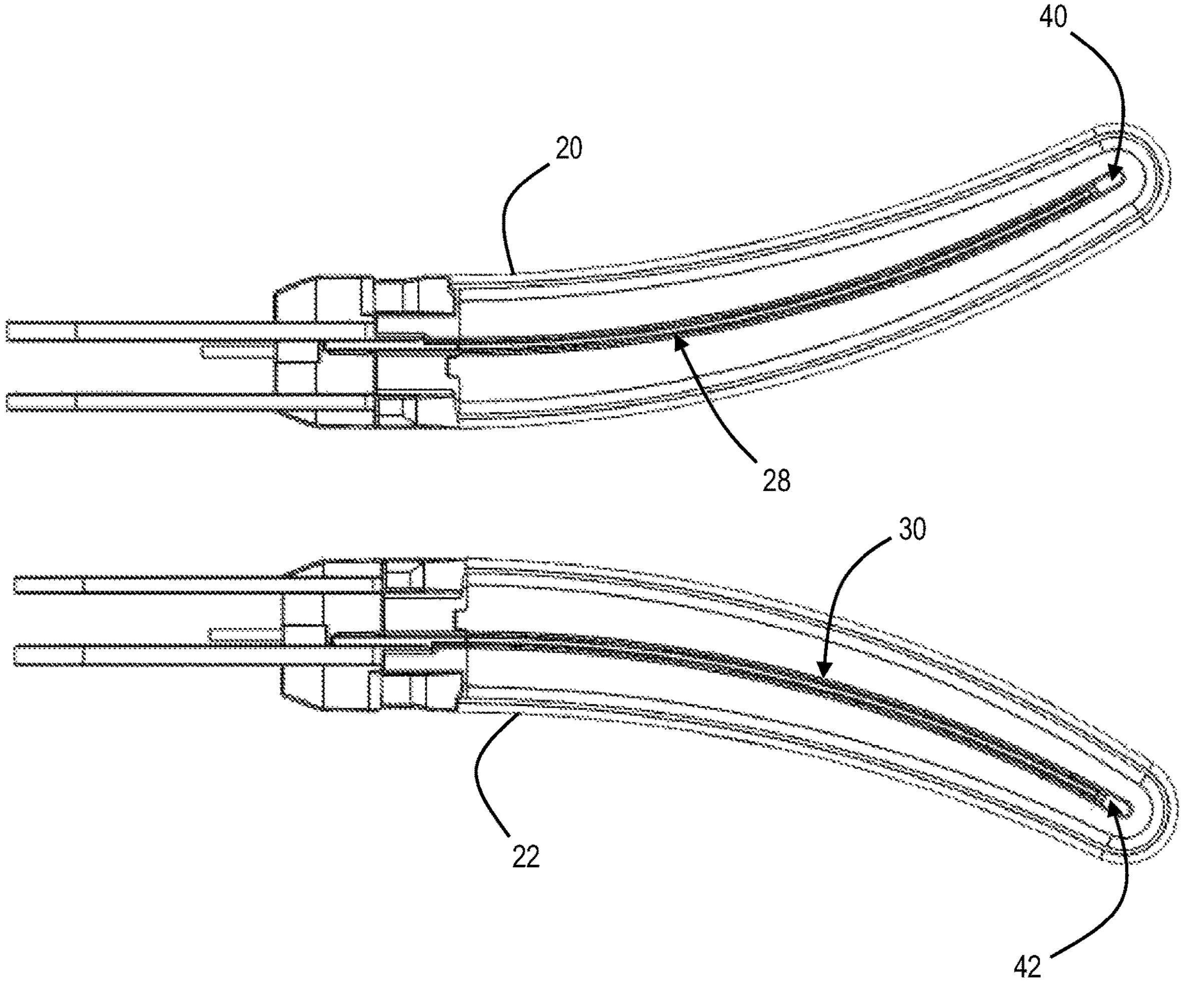
FIG. 4 is a bottom view of an upper jaw member and a top view of a lower jaw member according to the present invention.

As seen in FIGS. 3 and 4, opposing jaw members 20 and 22 include a pair of slots 40 and 42 positioned tangentially to tracks 28 and 30 at a distal end of jaw members 20 and 22 and in communication with tracks 28 and 30. As a result, movement of knife blade 50 distally within knife pathway will push any debris that has accumulated in tracks 28 and 30 distally to the ends of track 28 and 30 where the debris may be expelled out of slots 40 and 42 and away from vessel sealer 12 as knife blade 50 reaches the end of tracks 28 and 30. As seen in FIG. 4, slot 40 is in open communication with track 28, and slot 42 is in communication with track 30.

Figure 5:
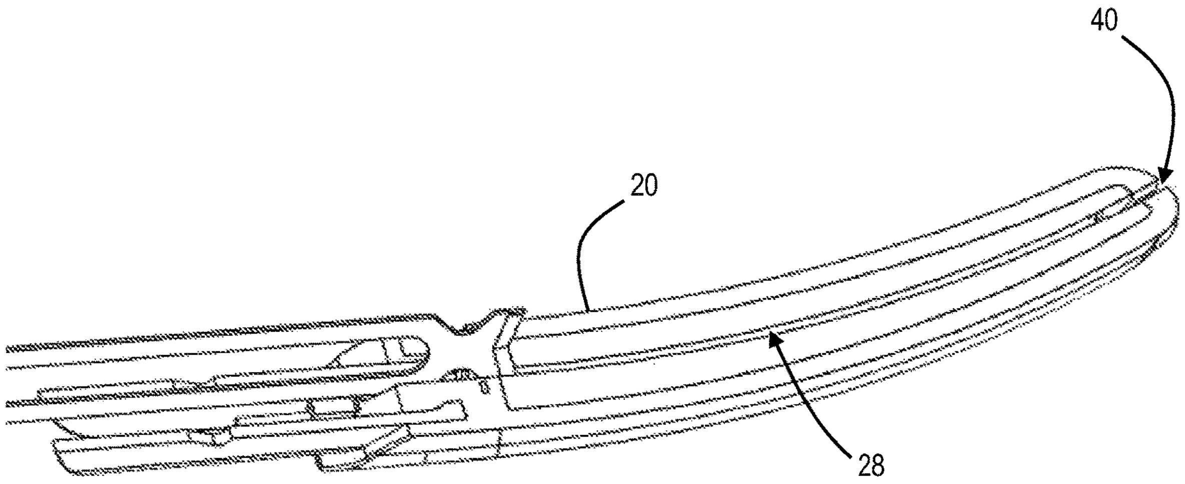
FIG. 5 is an isometric cross-sectional view of a jaw member according to the present invention.
Figure 6:
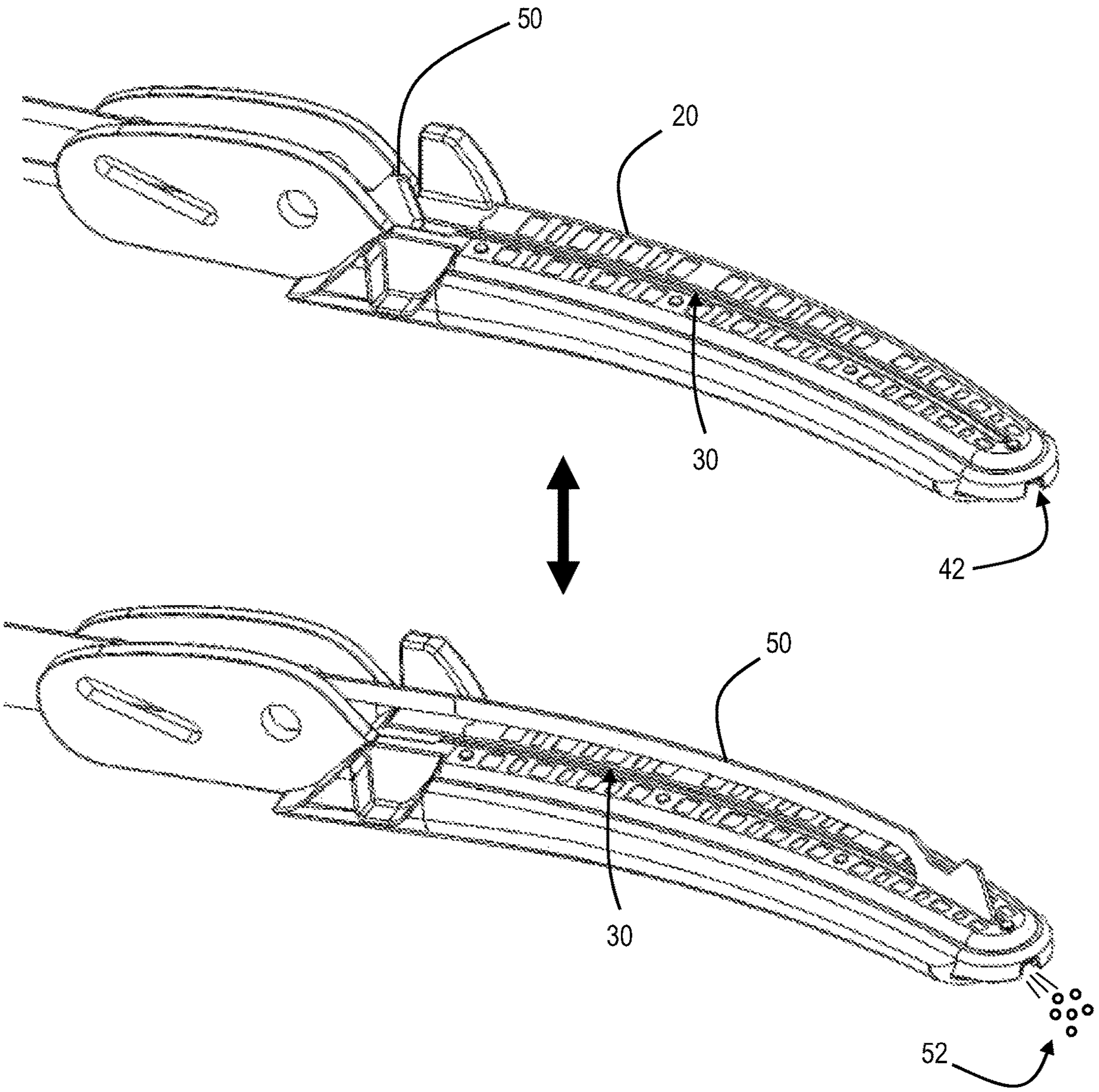
FIG. 6 is a perspective view of the of a jaw member according to the present invention showing movement of the knife blade expelling debris.
Figure 7:
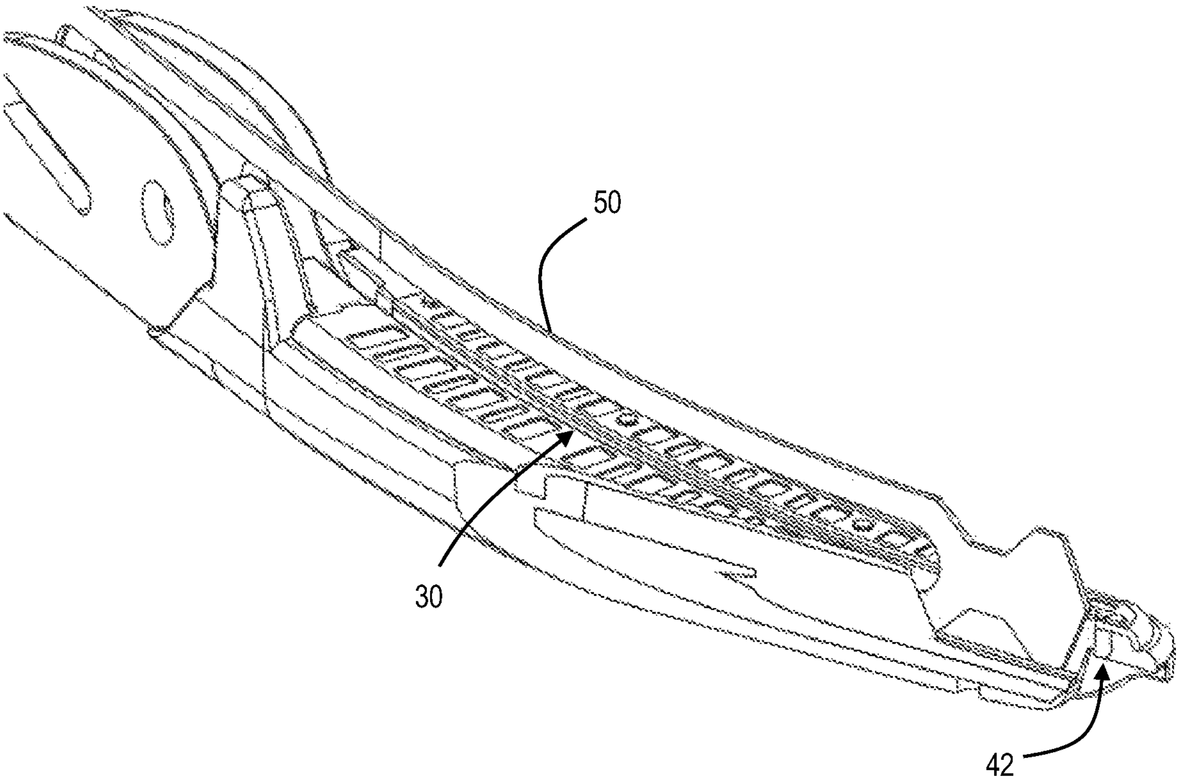
FIG. 7 is a partial cut-away view of a jaw member according to the present invention with the knife blade in the extended position.

As seen in FIG. 5, each of slot 40 and 42 is a continuation of each respective track 28 and 30, so that debris and foreign particles that build up in the knife pathway will be pushed through the knife pathway and out of slots 40 and 42 by the movement of knife blade 50 through the knife track. Referring to FIGS. 6 and 7, knife blade 50 may be extending in the knife pathway defined by tracks 28 and 30 to the end of knife pathway to eject any debris 52 that have accumulated in tracks 28 and 30 out of slots 40 and 42. Knife blade 50 can be extended to the ends of tracks 28 and 30 and the communication between the end of tracks 28 and 30 and slots 40 and 42, respectively, permits debris to be pushed into slots 40 and 42 by knife blade 50 and thus out of jaws 14.

Figure 8:
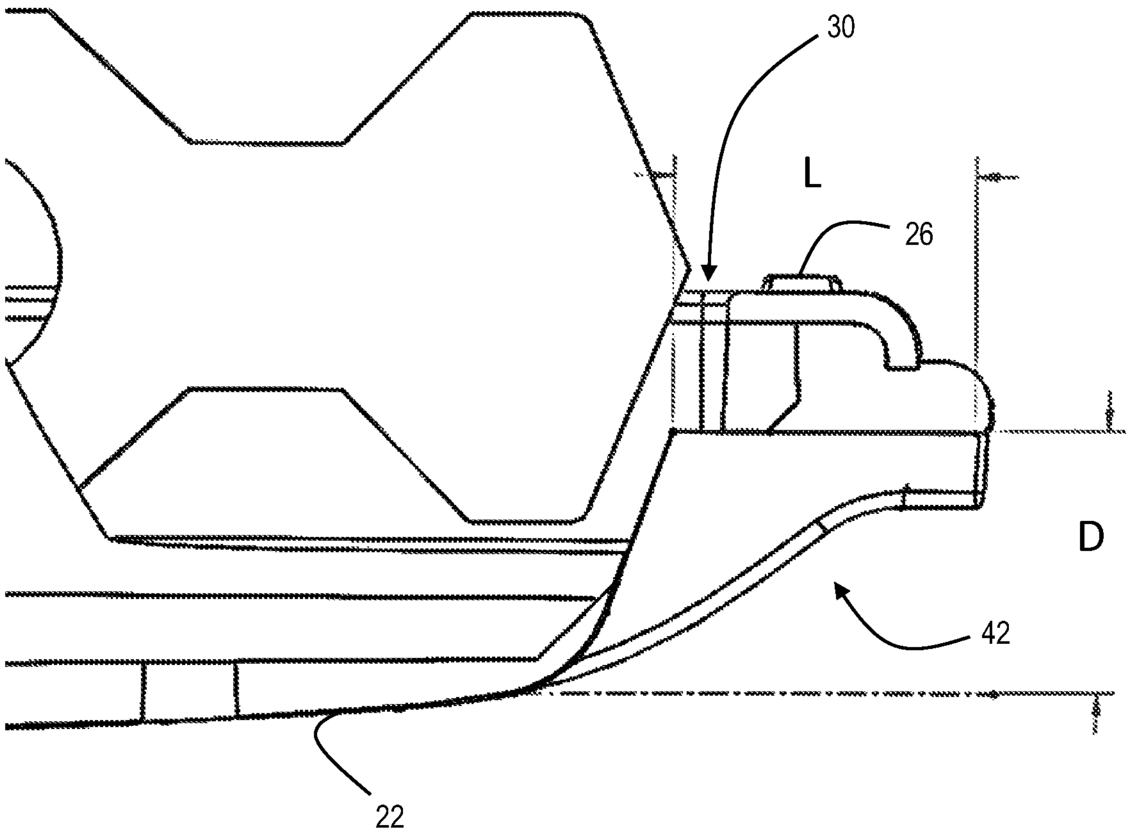
FIG. 8 is a longitudinal cross-section of a portion a jaw member according to the present invention with the knife blade in the extended position.
Figure 9:
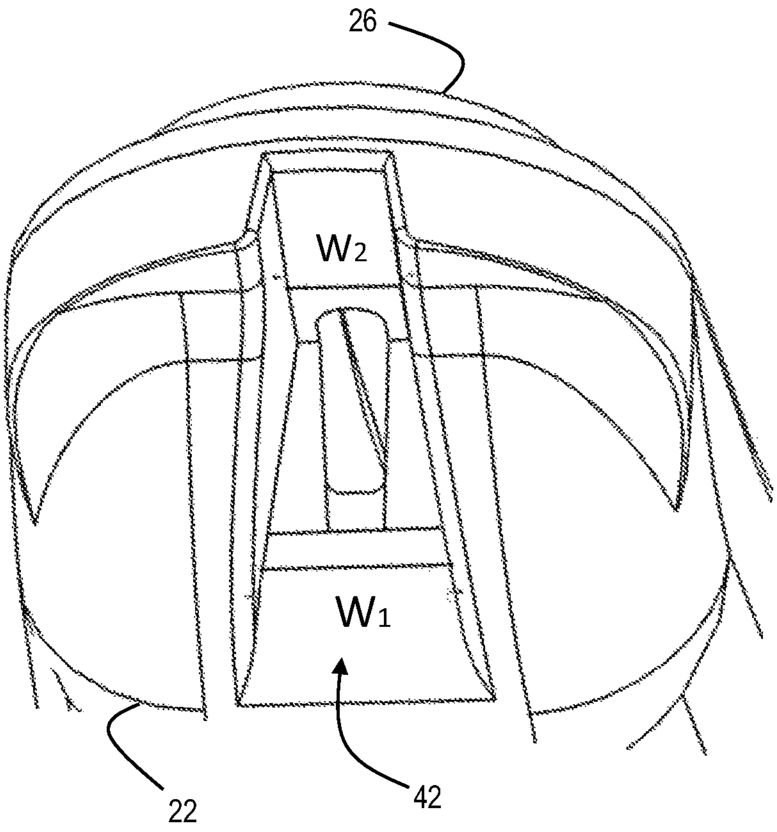
FIG. 9 is a perspective view of the distal end of a jaw member according to the present invention showing the slot for expelling debris.

Referring to FIG. 8, slots 40 and 42 are formed in the opposing portions of jaw members 20 and 22 from conductive faces 24 and 26 (only jaw member 22, conductive face 26, and slot 42 are shown for simplicity as the structure of opposing jaw member 20, and conductive face 24, and slot 40 mirror the structure shown). Slots 40 and 42 extend into jaw member 20 and 22 to communication with knife pathway formed by tracks 28 and 30. The depth (D) and length (L) of slots 40 and 42 are sufficient to allow for communication with slots 40 and 42 and the ejection of debris 52 when knife blade 50 extends to the end of the knife pathway formed by tracks 28 and 30. For example, in an exemplary vessel sealer 12 having conductive faces 24 and 26 with a length of 1.411 inches, D is 0.103 inches and L is 0.119 inches. L is thus less than ten percent of the length of conductive faces 24 and 26. As seen in FIG. 8, D represents approximately half or more of the overall depth of jaw members 20 and 22, and L is long enough to extend from the tip of vessel sealer 12 under conductive faces 24 and 26 to tracks 28 and 30. Referring to FIG. 9, slots 40 and 42 may vary in width from a wider portion W1 proximate to tracks 28 and 30 to a slightly narrower portion W2 at the tip of vessel sealer 12. In the example of a vessel sealer of having of jaw members 20 and 22 with a width of 0.231 inches proximate to wider portion W1 of slots 40 and 42, W1 may be 0.063 inches and W2 may be 0.038 inches, and thus may transition from about 30 percent of the overall width of jaw members 20 and 22 to about 16 percent of the overall width of jaw members 20 and 22.

What is claimed is:

1. A surgical instrument, comprising:

a pair of jaws having a first jaw member and a second jaw member that are pivotally mounted with respect to each other for movement between an open position and a closed position;

a first sealing surface supported by the first jaw member and having a first track formed therein that extends from a first open end to a first closed end;

a second sealing surface supported by the second jaw member and having a second track formed therein that extends from a second open end to a second closed end and that will align with the first track when the pair of jaws are in the closed position to define a knife pathway;

a first slow formed in a first distal end of the first jaw member that extends from a first tip of the first jaw member to penetrate through the first closed end of the first track so that the first slot is in communication with the first track; and a second slot formed in a second distal end of the second jaw that extends from a second tip of the second jaw member to penetrate through the second closed end of the second track so that the second slot is in communication with the second track.

2. The surgical instrument of claim 1, further comprising a knife blade positioned in the knife pathway and moveable in the knife pathway toward the first closed end of the first track and the second closed end of the second track.

3. The surgical instrument of claim 2, wherein movement of knife blade in the knife pathway will cause any debris in the knife pathway to be ejected from at least one of the first slot and the second slot.

4. The surgical instrument of claim 3, wherein the first slot and the second slot extend under the first sealing surface and the second sealing surface, respectively.

5. The surgical instrument of claim 4, wherein each of the first slot and the second slot have a first width proximate to a tip of the pair of jaws and a second width proximate to the first track and the second track that is wider than the first width.

6. The surgical instrument of claim 5, wherein the first slot and the second slot each have a depth that extends at least halfway through the first jaw member and the second jaw member, respectively.

7. The surgical instrument of claim 6, wherein the first track and the second track are curved.

8. The surgical instrument of claim 1, wherein the first slot is in communication with the first closed end of the first track and the second slot is in communication with the second closed end of the second track when the pair of jaws are in the open position and when the jaws are in a closed position and a knife is fully extended into the knife pathway.

9. A method of clearing debris from a surgical instrument, comprising:

providing a vessel sealer including pair of jaws formed by a first jaw member having a first sealing surface with a first track having a first closed end and a first slot formed in a first distal end of the first jaw member that extends from a first tip of the first jaw member to penetrate through the closed end of the first track to be in communication with the first track and a second jaw member having a second sealing surface with a second track having a second closed end and a second slot formed in a second distal end of the second jaw member that extends from a second tip of the second jaw member to penetrate through the closed end of the first track to be in communication with the second track; and extending a knife blade within the first track and the second track to push any debris out of the first slot and the second slot.

10. The method of claim 9, wherein the first slot and the second slot extend under the first sealing surface and the second sealing surface, respectively.

11. The method of claim 10, wherein the first slot and the second slot each have a first width proximate to a tip of the pair of jaws and a second width proximate to the first track and the second track that is wider than the first width.

12. The method of claim 11, wherein the first slot and the second slot each have a depth that extends at least halfway through the first jaw member and the second jaw member, respectively.

13. The method of claim 12, wherein the first track and the second track are curved.

14. The method of claim 9, wherein the first slot is in communication with the first closed end of the first track and the second slot is in communication with the second closed end of the second track during the step of extending a knife blade within the first track and the second track to push any debris out of the first slot and the second slot.

* * * * *